(12) United States Patent
Shambayati et al.

(10) Patent No.: US 11,559,594 B2
(45) Date of Patent: Jan. 24, 2023

(54) HYBRID FAR UV-C AND VISIBLE LAMP

(71) Applicants: Ali Shambayati, Carefree, AZ (US); Fatemeh Abnoosi, Paradise Valley, AZ (US)

(72) Inventors: Ali Shambayati, Carefree, AZ (US); Fatemeh Abnoosi, Paradise Valley, AZ (US)

(73) Assignees: Ali Shambayati, Carefree, AZ (US); Fatemeh Abnoosi, Paradise Valley, AZ (US)

( * ) Notice: Subject to any disclaimer, the term of this patent is extended or adjusted under 35 U.S.C. 154(b) by 0 days.

(21) Appl. No.: 17/356,573

(22) Filed: Jun. 24, 2021

(65) Prior Publication Data

US 2021/0402027 A1 Dec. 30, 2021

Related U.S. Application Data

(60) Provisional application No. 63/044,564, filed on Jun. 26, 2020.

(51) Int. Cl.
| | | |
|---|---|---|
| *A61L 2/10* | (2006.01) | |
| *A61L 2/08* | (2006.01) | |
| *F21S 9/02* | (2006.01) | |
| *F21V 23/04* | (2006.01) | |
| *A61L 2/26* | (2006.01) | |
| *F21Y 113/00* | (2016.01) | |
| *F21Y 115/10* | (2016.01) | |

(52) U.S. Cl.
CPC ........ *A61L 2/10* (2013.01); *A61L 2/26* (2013.01); *F21S 9/02* (2013.01); *F21V 23/0442* (2013.01); *A61L 2202/11* (2013.01); *F21Y 2113/00* (2013.01); *F21Y 2115/10* (2016.08)

(58) Field of Classification Search
CPC ......... A61L 2/10; A61L 2/084; F21V 23/0442
See application file for complete search history.

(56) References Cited

U.S. PATENT DOCUMENTS

| | | | |
|---|---|---|---|
| 7,808,170 B2 | 10/2010 | Justel et al. | |
| 8,350,228 B2 | 1/2013 | Welker | |
| 8,975,605 B2 | 3/2015 | Neister | |
| 10,556,025 B2 | 2/2020 | Ufkes | |
| 10,767,843 B2 | 9/2020 | Weeks, Jr. et al. | |
| 2013/0317422 A1* | 11/2013 | Levenson | A61M 5/142 604/67 |
| 2017/0080117 A1* | 3/2017 | Gordon | A61L 2/10 |
| 2017/0321877 A1* | 11/2017 | Polidoro | F21V 33/0088 |
| 2018/0311386 A1* | 11/2018 | Hawkins | F21V 29/70 |
| 2018/0320872 A1 | 11/2018 | Weeks, Jr. et al. | |
| 2020/0178573 A1 | 6/2020 | Naito | |
| 2020/0261608 A1* | 8/2020 | Crosby | A61L 2/10 |
| 2020/0408394 A1* | 12/2020 | Weeks, Jr. | F21S 8/03 |

* cited by examiner

*Primary Examiner* — Kevin Joyner
(74) *Attorney, Agent, or Firm* — Xsensus LLP (57) ABSTRACT

A solid-state lamp includes a first plurality of solid-state emitters that emit light at visible wavelengths and a second plurality of solid-state emitters that emit light at a safe ultraviolet wavelength, wherein the second plurality of solid-state emitters emit light at least when the first plurality of solid-state emitters emit light.

20 Claims, 8 Drawing Sheets

HYBRID FAR UV-C AND VISIBLE LAMP

CROSS-REFERENCE TO RELATED APPLICATIONS

This patent application claims the benefit of and priority to U.S. Provisional Patent Application No. 63/044,564, titled "UV-C AND TUNABLE VISIBLE LED BULB," filed on Jun. 26, 2020, which is herein incorporated by reference in its entirety.

FIELD

The present disclosure is directed generally to lamps, and more particularly to lamps that can provide a more hygienic environment.

BACKGROUND

Ultraviolet (UV) light has been shown to sanitize as well as prohibit germ and mold growth. Numerous current lamps employ a plurality of light emitting diodes (LEDs) that output light at different wavelengths. UV light has been shown to sanitize as well as prohibit germ and mold growth, but most UV wavelengths employed may have significant negative consequences for mammals, such that it cannot be deployed when mammals are present. Typically, germicidal lamps generate UV-C at 254 nm for sterilization, but this wavelength is not safe for mammals. Thus, current systems that employ both UV light and visible light are controlled based on determining whether or not a microbe could be present and whether or not the space is occupied.

SUMMARY

One or more embodiments are directed to a lamp that supply both safe UV-C light and visible light simultaneously and may be used in conventional lighting devices.

One or more embodiments are directed to a solid-state lamp that includes a first plurality of solid-state emitters that emit light at visible wavelengths and a second plurality of solid-state emitters that emit light at a safe ultraviolet wavelength, wherein the second plurality of solid-state emitters emit light at least when the first plurality of solid-state emitters emit light.

The second plurality of solid-state emitters may be controlled to continuously emit safe ultraviolet wavelength.

The solid-state lamp may include a third solid-state emitter to emit nightlight light to indicate that the second plurality of solid-state emitters still emit light when the first plurality of solid-state emitters is off.

The solid-state lamp, further including a back-up power supply to the second plurality of solid-state emitters to continue emit light even when the lamp is turned off, such as a rechargeable battery.

The solid-state lamp may include circuitry configured to compare an intensity of light emitted from the second plurality of solid-state emitters to a predetermined intensity that is sufficient to provide a selected hygienic level to an ambient environment.

The solid-state lamp may include circuitry configured to compare an intensity of light emitted from the second plurality of solid-state emitters to a predetermined intensity that is sufficient to provide a selected hygienic level to an ambient environment, i.e., to provide a feedback loop insuring the efficacy of the ultraviolet light for a selected hygienic level. The circuitry may determine that the intensity of light emitted from the second plurality of solid-state emitters is less than the predetermined intensity, the circuitry is configured to output a warning. Outputting the warning may include at least one of sending a message to a mobile device associated with the lamp; controlling the first plurality of solid-state emitters to emit light a particular color; controlling the first plurality of solid-state emitters to emit light discontinuously; and stopping the first plurality of solid-state emitters from emitting.

A photodetector may be provided to detect the intensity of light output by the second plurality of solid-state emitters and to output detected intensity to the circuitry.

A reflective surface of the light bulb may be provided to direct and focus the light output of the second plurality of solid-state emitters onto the UV detector, used in a feedback loop for monitoring sufficient output levels of the selected hygienic levels.

The second plurality of solid-state emitters may be in a periphery of the solid-state lamp or may be alternately arranged with the first plurality of solid-state emitters.

The solid-state lamp may have more solid-state emitters in the second plurality of solid-state emitters than in the first plurality of solid-state emitters.

The second plurality of solid-state emitters and the first plurality of solid-state emitters may be in a same plane.

One or more embodiments are directed to a method of providing a selected hygienic level to and illumination of an ambient environment including emitting, via a first plurality of solid-state emitters in the solid-state lamp, light at visible wavelengths; and emitting, via second plurality of solid-state emitters in the solid-state lamp, light at a safe ultraviolet wavelength, at least when the first plurality of solid-state emitters emit light. The safer ultraviolet light may be provided at a predetermined intensity and duration that is sufficient to provide the selected hygienic level to the ambient environment.

DETAILED DESCRIPTION

Recent research has proven that direct and repetitive illumination from 222 nm (far-UVC range), which is a powerful disinfectant, does not cause adverse reactions in mammals, e.g., eye damage, skin cancer, and so forth. At this particular wavelength, a lower dose to achieve sanitization is required than for traditional UV-C wavelengths, increasing efficiency, and pathogens may be killed in seconds, versus minutes with traditional UV-C wavelengths. The intensities and duration needed may be predetermined experimentally for different ambient conditions, areas, and selected level of hygienic conditions, including sanitization, disinfection, and sterilization, as a scenario demands. Further, this wavelength does not penetrate human skin. As known in the art, LEDs are tunable to different wavelengths, low-cost, power efficient, and have long lifetime.

Embodiments are directed to provided hybrid light bulbs based on safe and effective UV-C LEDs, i.e., far UV-C LEDs, to be used in any and all conventional future light fixtures. The new light bulbs will be "hybrid"; i.e., include both safe UV-C LEDs, e.g., 222-nm LEDs, and visible LEDs. Such safe UV-C LEDs may include those manufactured by Shenzhen Suntech Company Limited. The new "Hybrid UV-222™" bulbs may be provided in various form factors and to retrofit existing or custom fixtures as drop-in replacements. The UV LEDs and visible LEDs may be arranged in any combination or configuration on the same substrate, e.g., a printed circuit board, thus producing a hybrid lamp and the visible LEDs may be any color or combination of colors to address the needs for different spaces. Since LED power consumption is very low, the far UV-C LED of the hybrid light may be used continuously.

Figure 1:
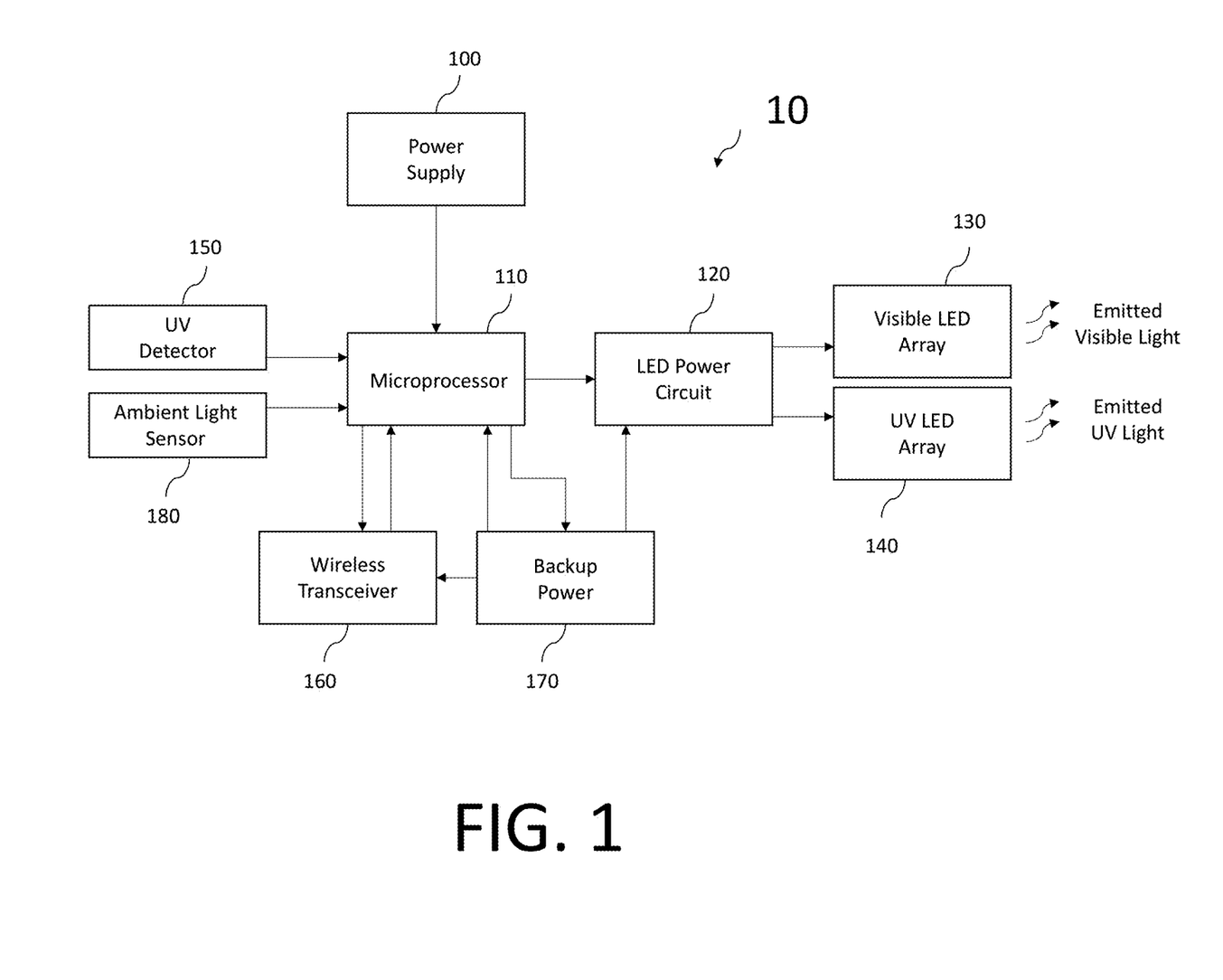
FIG. 1 illustrates a schematic view of a lighting system in accordance with an embodiment.

FIG. 1 illustrates a schematic view of components of a lamp 10, e.g., a solid-state lamp, in accordance with an embodiment. As may be seen therein, the lamp 10 may include a power supply 100, a microprocessor 110, an LED power circuit 120, a visible LED array 130 that emits visible light, a UV LED array 140 that emits UV-C light, a UV detector 150, a wireless transceiver 160, a backup power supply 170, and an ambient light sensor 180.

Figure 2A:
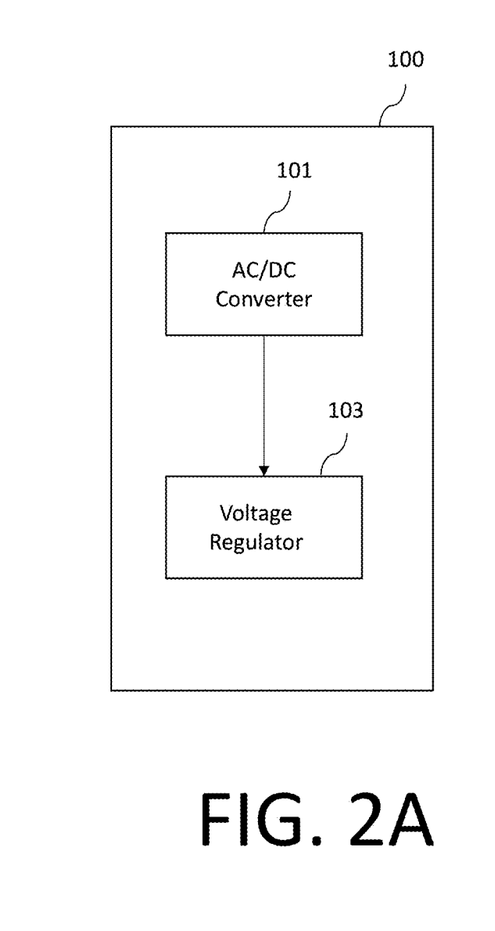
FIGS. 2A and 2B illustrates schematic view of different power supplies in accordance with embodiments.
Figure 2B:
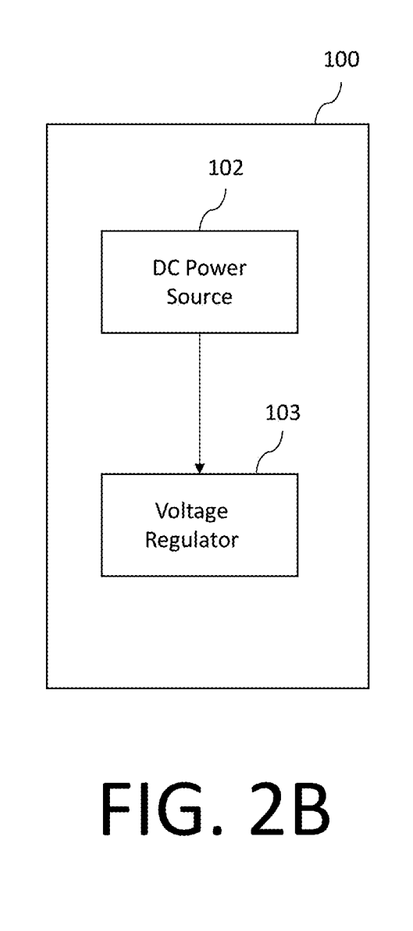

FIGS. 2A and 2B respectively illustrate a schematic view of a power supply 100a and a power supply 100b for use as the power supply 100. The power supply 100a may include and AC/DC converter 101 and a voltage regulator 103. The power supply 100b may include a DC power source 102 and the voltage regulator 103.

Figure 3A:
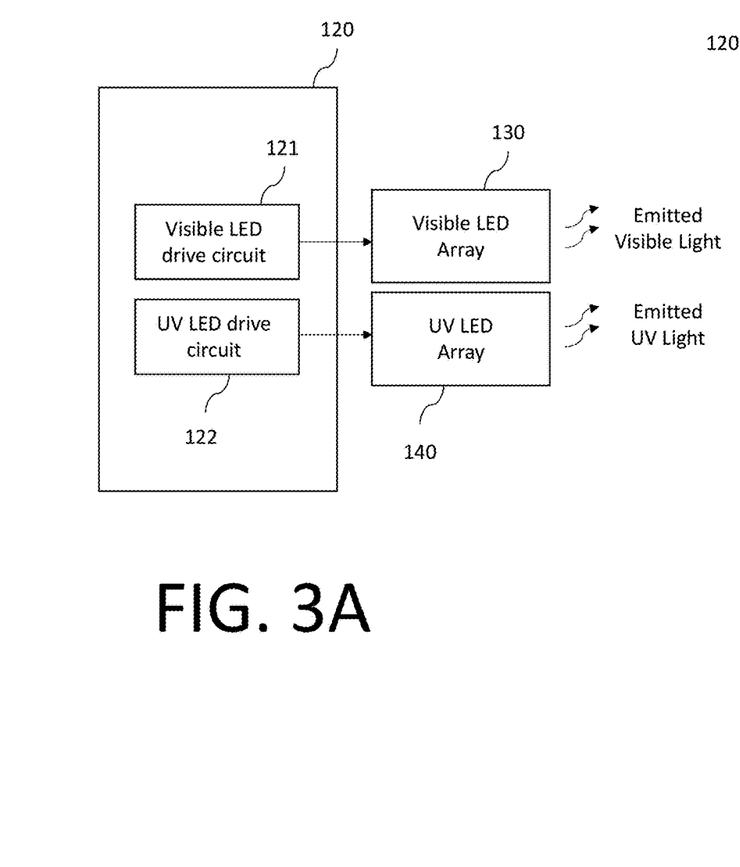
FIGS. 3A and 3B illustrate schematic views of an LED power circuit in accordance with an embodiment.
Figure 3B:
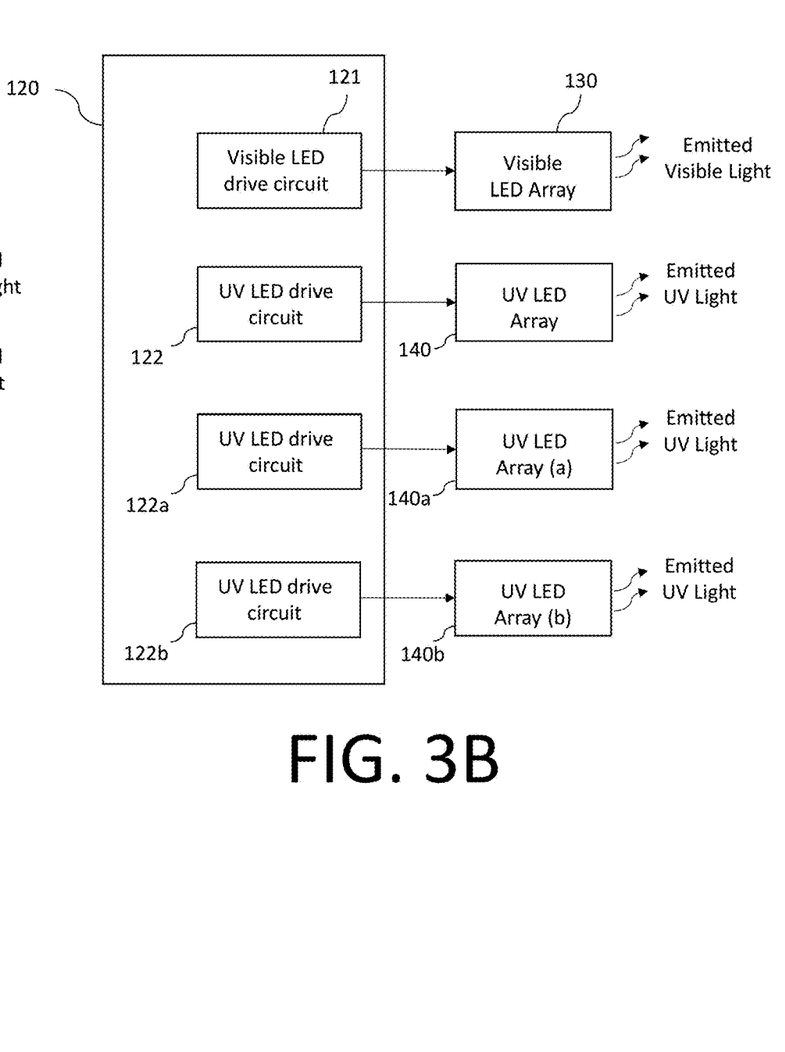

FIGS. 3A and 3B illustrate schematic views of the LED power circuit 120 in accordance with an embodiment. As may be seen therein, the LED power circuit 120 may include a visible LED drive circuit 121 that drives the visible LED array 130 and a UV LED drive circuit 122 that drives the UV LED array 140.

Figure 4:
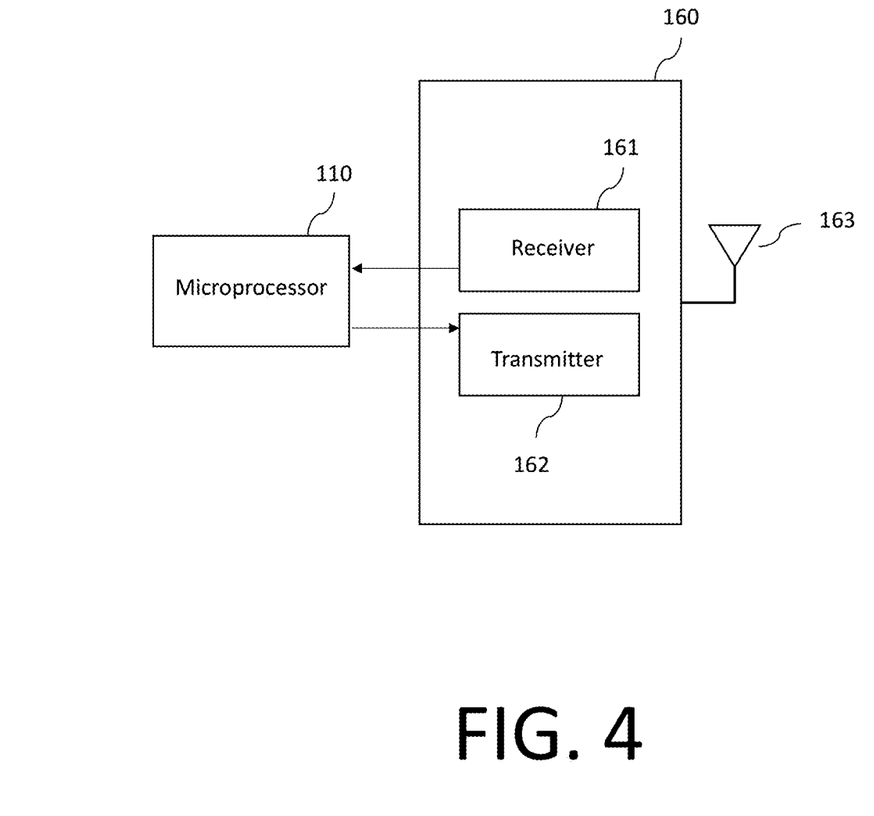
FIG. 4 illustrates a schematic view of a wireless transceiver in accordance with an embodiment.

FIG. 4 illustrates a schematic view of the wireless transceiver 160 in accordance with an embodiment. As may be seen therein, the wireless transceiver 160 may include an antenna 163, a receiver 161 in communication with the antenna 163 and the microprocessor 110, and a transmitter 162 in communication with the antenna 163 and the microprocessor 110. The wireless transceiver 160 may employ Bluetooth technology, RF technology, or any other appropriate wireless communication technology to communicate with a remote device or an app.

Figure 5:
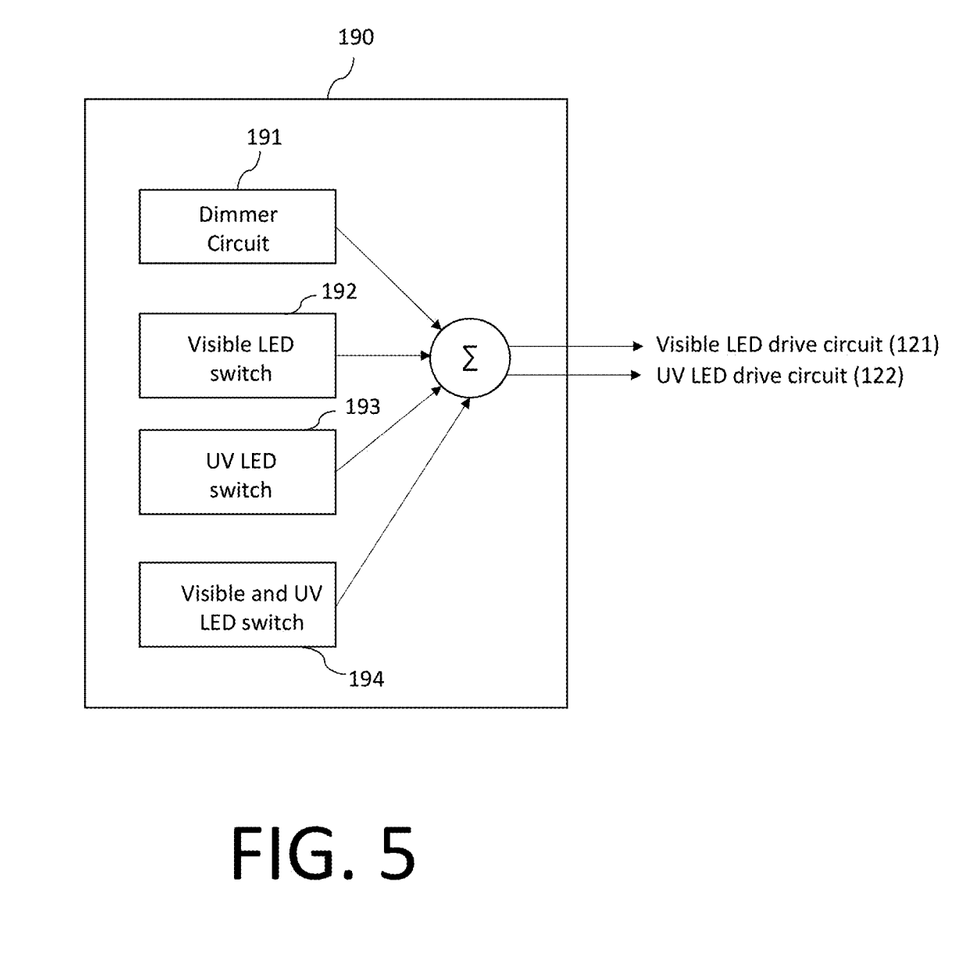
FIG. 5 illustrates a control for use with the lamp 10 in accordance with an embodiment.

FIG. 5 illustrates a control 190 for use with the lamp 10 in accordance with an embodiment. The remote control 190 may include a visible dimmer circuit 191, a visible (individual) LED switch 192, a UV (individual) LED switch 193, and a visible and UV (simultaneous) LED switch 194. The signals from the circuits may be summed and output to the appropriate ones of the visible LED drive circuit 121 and the UV LED drive circuit 122 via the microprocessor 110. Similarly, a UV dimmer circuit may be included to set different levels of hygiene desired. A motion sensor may be provided to automatically turn on any or all of the switches. Alternatively, the control 190 may not include an individual control of the UV LED such that the UV LED array may automatically be turned on/off automatically when the visible light is turned on/off or may always be on. As a further alternative, the control 190 may include a timer that may be set to automatically turn on the visible LED array to a set time and to automatically turn on the UV LED array at the same time or for a predetermined time before the visible LED array is set to turn on.

Figure 8A:
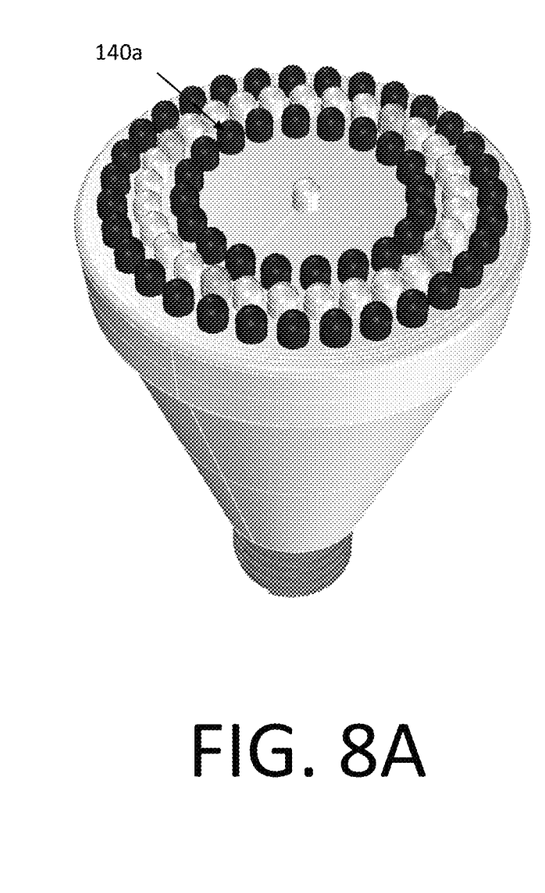
FIGS. 8A and 8B illustrate views of a lamp according to an embodiment.
Figure 8B:
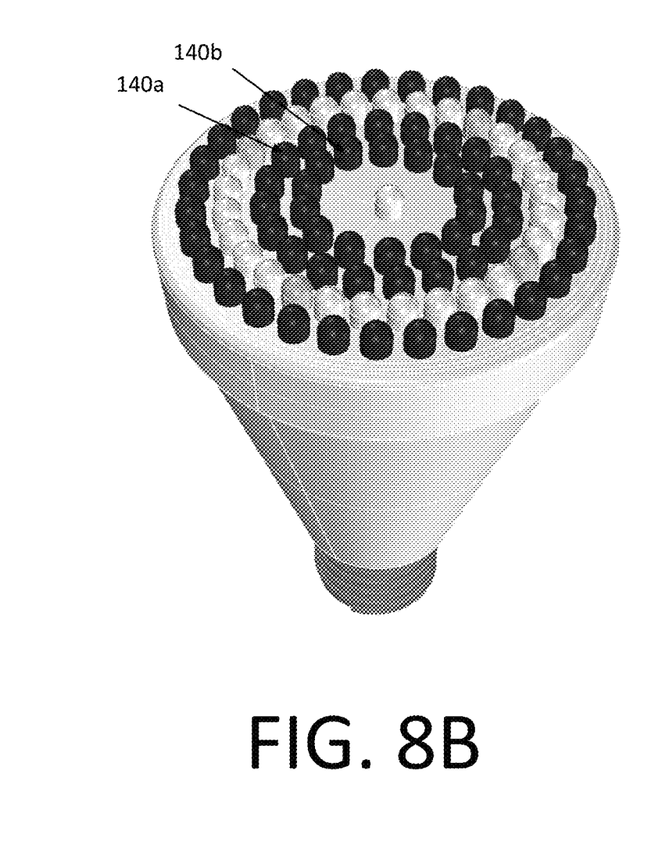

Also, if the UV LED has a life expectancy that either continuous use thereof, or concurrent use only with the visible LEDs, would result in the UV LED array dying before the visible LED array, a number of compensating features may be included. For example, the second plurality of solid-state emitters may include multiple banks of more UV LEDs 140a and 140b, etc., as shown in FIGS. 8A and 8B, than are needed, i.e. redundant UV LEDs, some of which are switched on when other UV LEDs die. Additionally or alternatively, the intensity and/or duration of the UV LED array may be controlled to provide the selected level of hygiene, e.g., the UV LED array may intermittently output UV light sufficient to obtain the selected level of hygiene and/or may control an intensity of UV light sufficient to obtain the selected level of hygiene.

Additionally, as shown, e.g., in FIGS. 8A and 8B, the second plurality of solid-state emitters may include multiple UV LED banks, 140, 140a, 140b, etc., for the purpose of selectively producing higher intensity output. Since achieving hygienic conditions is proportional to square footage and UV intensity and exposure time, second UV LED bank 140a, third UV LED bank 140b, etc. may be added to reduce the time to reach desired hygienic conditions by producing higher intensity at shorter intervals. For example, the first bank of UV LEDs 140 is sufficient to reach hygienic conditions based on the number of people that are normally present in a room, but when that number increases, e.g., a house party or large gatherings in an office room during meetings, the second and/or third bank of UV LEDs 140a and 140b may be switched on via the mobile app or a secondary mechanism on the outlet switch, to accommodate the higher traffic.

The backup power supply 170 may be battery, a rechargeable battery, a capacitor, and so forth. When the power supply 100 is lost or switched off, the backup power supply 170 may continue to power the microprocessor 110 and LED power circuit 120. For example, when the main power 100 is disconnected, the microprocessor 110 may automatically activate the backup power source 170 to keep the UV LEDs 140 on via the UV LED driver circuit 122. The microprocessor 110 may also control the backup power supply 170 to power the wireless transceiver 160 to communicate to a remote device or app that the lamp 10 is running on backup power.

In addition to or alternatively to the control 190, the wireless transceiver 160 may provide input to the microprocessor 110 to turn on/off or otherwise control the visible LEDs 130 and/or UV LEDs 140. The microprocessor 110 provides the status of the LEDs to a remote receiver such as a mobile app, an IoT (Internet of Things) device, or a computer, which in turn enables the user to control the lights from a remote location.

The UV detector 150 may continuously monitor the output of the UV LEDs 140 and may provide a detected intensity as feedback regarding the performance of the UV LEDs 140 to the microprocessor 110. If the UV light intensity drops below a certain threshold and/or duration needed for effective hygiene, the microprocessor 110 may activate any number of signaling schemes, e.g., flashing or changing the color of the visible LEDs 130, sending a signal via the wireless transmitter 160 to a remote device, stopping the visible LEDs from outputting light, and so forth. The UV detector 150 may be an onboard sensor that resides inside the lamp 10 and normalized for covering specific ambient area and/or may be externally located where the incident UV light is measured at some distance away from the lamp 10, e.g., a surface or object to have the desired hygienic conditions.

The ambient light sensor 180 may provide information about ambient light to the microprocessor 110. The microprocessor 110 may control the visible LED drive circuit 121 to output visible light from a subset of the visible LED array 130 or from an independent LED or LED array to indicate that the UV LED array 140 is continuing to output UV light at a sufficient level even when the visible light is not being used.

Figure 6A:
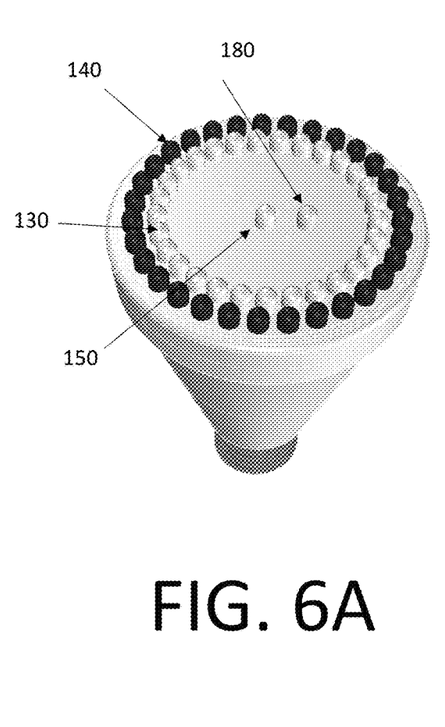
FIGS. 6A to 6C illustrate views of a lamp according to an embodiment.
Figure 6B:
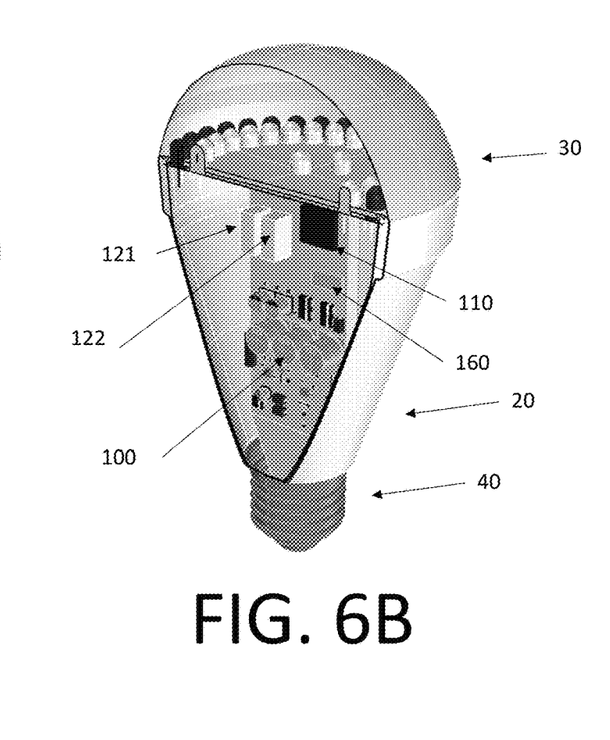
Figure 6C:
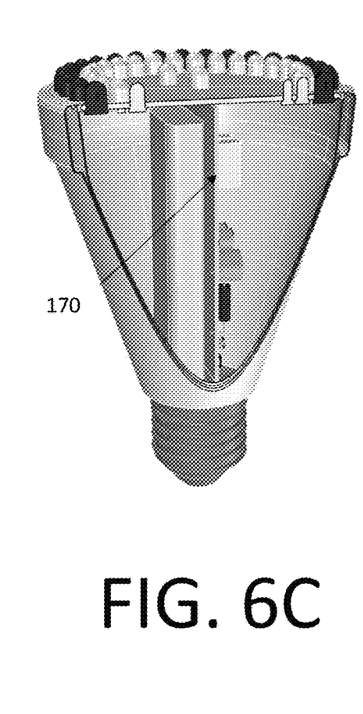

FIG. 6A illustrates a perspective top view of the lamp 10 in accordance with an embodiment. FIG. 6B illustrates a perspective cross-sectional view of a first side of the lamp 10 in accordance with an embodiment. FIG. 6C illustrates a perspective cross-sectional view of a second side of the lamp 10, opposite the first side, in accordance with an embodiment. The lamp 10 also includes a body 20, an optic 30 that outputs light from the LED arrays and a base 40 to be coupled to a light bulb base. The material, geometry, and dimensions of the body 20, the optic 30, and the base 40 may be of any standard, custom, or proprietary configuration, for a given target application or end-use.

Figure 7A:
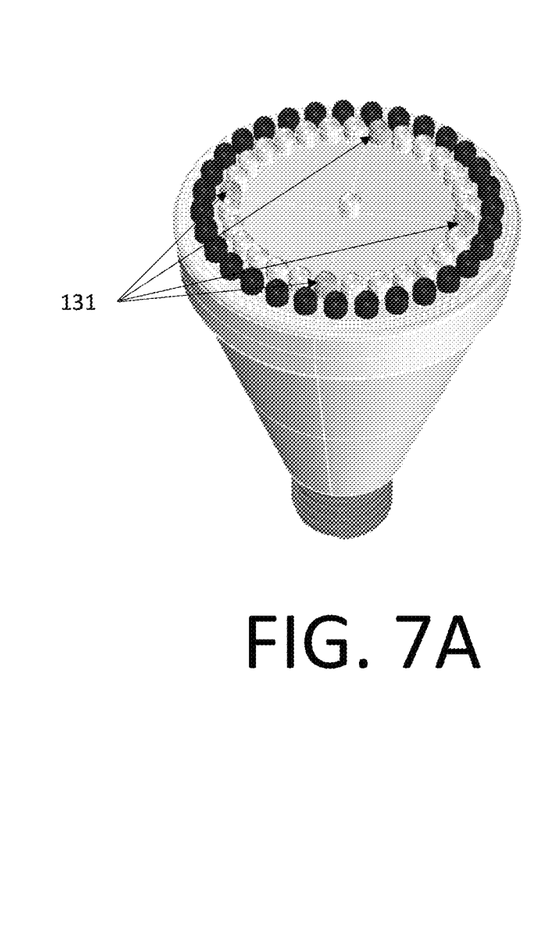
FIGS. 7A and 7B illustrate views of a lamp according to an embodiment.
Figure 7B:
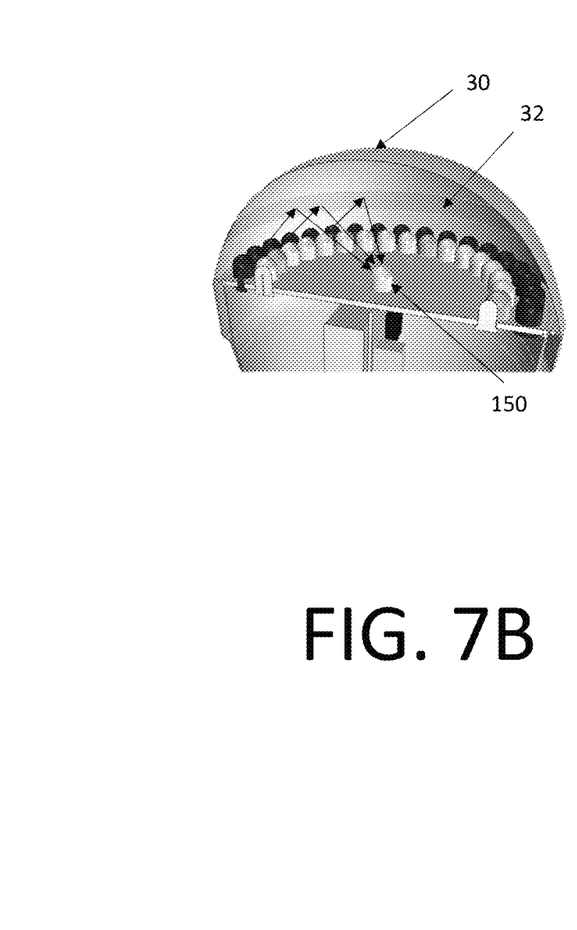

FIG. 7A illustrates a perspective top view of a lamp 10A in accordance with an embodiment, in which separate LEDs 131 are used for the nightlight function as noted above. FIG. 7B illustrates a perspective cross-sectional view of a second side of the lamp 10A in accordance with an embodiment, in which the optic 30 includes a reflective portion 32, e.g., a ring or a partial reflector that does not interfere with significantly with the output of the UV LED, that may direct a portion of the UV light output from the UV LED array onto the UV detector 150 to insure that sufficient UV light is being output form the UV LED array to realize the desired hygienic conditions.

Example embodiments have been disclosed herein, and although specific terms are employed, they are used and are to be interpreted in a generic and descriptive sense only and not for purpose of limitation. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise indicated. Accordingly, various changes in form and details may be made without departing from the spirit and scope of the embodiments set forth in the claims.

What is claimed is:

1. A solid-state lamp, comprising:
a first plurality of solid-state emitters that emit light at visible wavelengths to illuminate an ambient environment with visible light; and
a second plurality of solid-state emitters that emit light at an ultraviolet wavelength that does not penetrate human skin, wherein the second plurality of solid-state emitters emit light at least when the first plurality of solid-state emitters emit light at a same intensity regardless whether or not the ambient environment is illuminated with visible light, even when a human is present and illuminate the ambient environment with ultraviolet light to provide hygienic conditions to the ambient environment during visible light illumination of the ambient environment.

2. The solid-state lamp of claim 1, wherein the second plurality of solid-state emitters continuously emit light.

3. The solid-state lamp of claim 2, further comprising a third solid-state emitter to emit nightlight light to indicate that the second plurality of solid-state emitters still emit light when the first plurality of solid-state emitters is off.

4. The solid-state lamp of claim 2, further comprising a back-up power supply to the second plurality of solid-state emitters to continue emit light even when the solid-state lamp is turned off.

5. The solid-state lamp of claim 4, wherein the back-up power supply includes a rechargeable battery.

6. The solid-state lamp of claim 1, further comprising circuitry, configured to compare an intensity of light emitted from the second plurality of solid-state emitters to a predetermined intensity that is sufficient to provide a desired level of hygiene for the ambient environment.

7. The solid-state lamp of claim 6, wherein, when the circuitry determines that the intensity of light emitted from the second plurality of solid-state emitters is less than the predetermined intensity, the circuitry is configured to output a warning.

8. The solid-state lamp of claim 7, wherein, when outputting the warning, the circuitry is configured to perform at least one of:
sending a message to a mobile device associated with the lamp,
controlling the first plurality of solid-state emitters to emit light a particular color,
controlling the first plurality of solid-state emitters to emit light discontinuously, and
stopping the first plurality of solid-state emitters from emitting.

9. The solid-state lamp of claim 6, further comprising a photodetector to detect the intensity of light output by the second plurality of solid-state emitters and to output detected intensity to the circuitry.

10. The solid-state lamp of claim 9, further comprising a reflective surface to direct light output by the second plurality of solid-state emitters to the photodetector.

11. The solid-state lamp of claim 6, wherein the circuitry is further configured to receive the intensity of light emitted from the second plurality of solid-state emitters from a detector in the ambient environment.

12. The solid-state lamp of claim 1, wherein the second plurality of solid-state emitters are in a periphery of the solid-state lamp.

13. The solid-state lamp of claim 1, wherein the second plurality of solid-state emitters are alternately arranged with the first plurality of solid-state emitters.

14. The solid-state lamp of claim 1, wherein there are more solid-state emitters in the second plurality of solid-state emitters than in the first plurality of solid-state emitters.

15. The solid-state lamp of claim 1, wherein the second plurality of solid-state emitters and the first plurality of solid-state emitters are in a same plane.

16. The solid-state lamp of claim 1, wherein the second plurality of solid-state emitters are light emitting diodes output 222 nm.

17. The solid-state lamp of claim 1, wherein the second plurality of solid-state emitters emit UVC light.

18. The solid-state lamp of claim 1, wherein the second plurality of solid-state emitters emit light at least whenever the first plurality of solid-state emitters emit light.

19. The solid-state lamp of claim 1, wherein the second plurality of solid-state emitters emit light at least when motion is sensed by a motion sensor.

20. A method of providing hygienic conditions to and illuminating a region with a solid-state lamp, the method comprising:

emitting, via a first plurality of solid-state emitters in the solid-state lamp, light at visible wavelengths to illuminate an ambient environment with visible light; and     emitting, via second plurality of solid-state emitters in the solid-state lamp, light at an ultraviolet wavelength that does not penetrate human skin, at least when the first plurality of solid-state emitters emit light at a same intensity regardless whether or not the ambient environment is illuminated with visible light, even when a human is present and illuminate the ambient environment with ultraviolet light to provide hygienic conditions to the ambient area during visible light illumination of the ambient environment.

\* \* \* \* \*